United States Patent [19]

Mesrobian et al.

[11] Patent Number: 5,647,843
[45] Date of Patent: Jul. 15, 1997

[54] ANTI-REFLUX URETERAL STENT

[75] Inventors: Hrair-George O. Mesrobian, Milwaukee, Wis.; Frederick D. Roemer, Bloomington, Ind.

[73] Assignee: Vance Products Incorporated, Spencer, Ind.

[21] Appl. No.: 653,409

[22] Filed: May 24, 1996

[51] Int. Cl.$^6$ ................................................. A61M 5/00
[52] U.S. Cl. ................................................. 604/8; 604/10
[58] Field of Search ................................. 604/8–10, 280, 604/54, 281, 282, 283, 284

[56] References Cited

U.S. PATENT DOCUMENTS

| | | | |
|---|---|---|---|
| 4,212,304 | 7/1980 | Finney . | |
| 4,610,657 | 9/1986 | Densow . | |
| 4,713,049 | 12/1987 | Carter | 604/8 |
| 4,790,809 | 12/1988 | Kuntz | 604/8 |
| 4,790,810 | 12/1988 | Pugh, Jr. et al. | 604/8 |
| 4,874,360 | 10/1989 | Goldberg et al. | 604/8 |
| 4,957,479 | 9/1990 | Roemer . | |
| 4,990,133 | 2/1991 | Solazzo . | |
| 5,116,309 | 5/1992 | Coll | 604/8 |
| 5,364,340 | 11/1994 | Coll . | |
| 5,380,270 | 1/1995 | Ahmadzadeh . | |
| 5,417,657 | 5/1995 | Hauer . | |

*Primary Examiner*—John G. Weiss
*Assistant Examiner*—Ki Yong O
*Attorney, Agent, or Firm*—Richard J. Godlewski

[57] ABSTRACT

Ureteral stents are tubes which are placed in the ureter between the bladder and kidney to maintain patency when otherwise due to stone burden, invasive tumor, scarring, or whenever the ureter has become obstructed in order to provide drainage of urine from the kidney to the bladder. In the past, stents of this nature are open ended tubes and may allow for the reflux of urine back into the kidney when there is sufficient buildup of pressure within the bladder. Since urine is generally considered to be sterile when within the body, this is generally not a problem. However, if the patient has a bladder infection and/or pyrogens are present, then urine refluxed into the ureter and kidney may result in the development of sepsis in the patient and cause serious illness and even death. The stent of the present invention has a very specific design and avoids this problem by providing a stent having a closed section, i.e., the bladder end section does not contain any fluid passageways and also comprises a means for retaining the stent within the bladder after implantation.

14 Claims, 2 Drawing Sheets

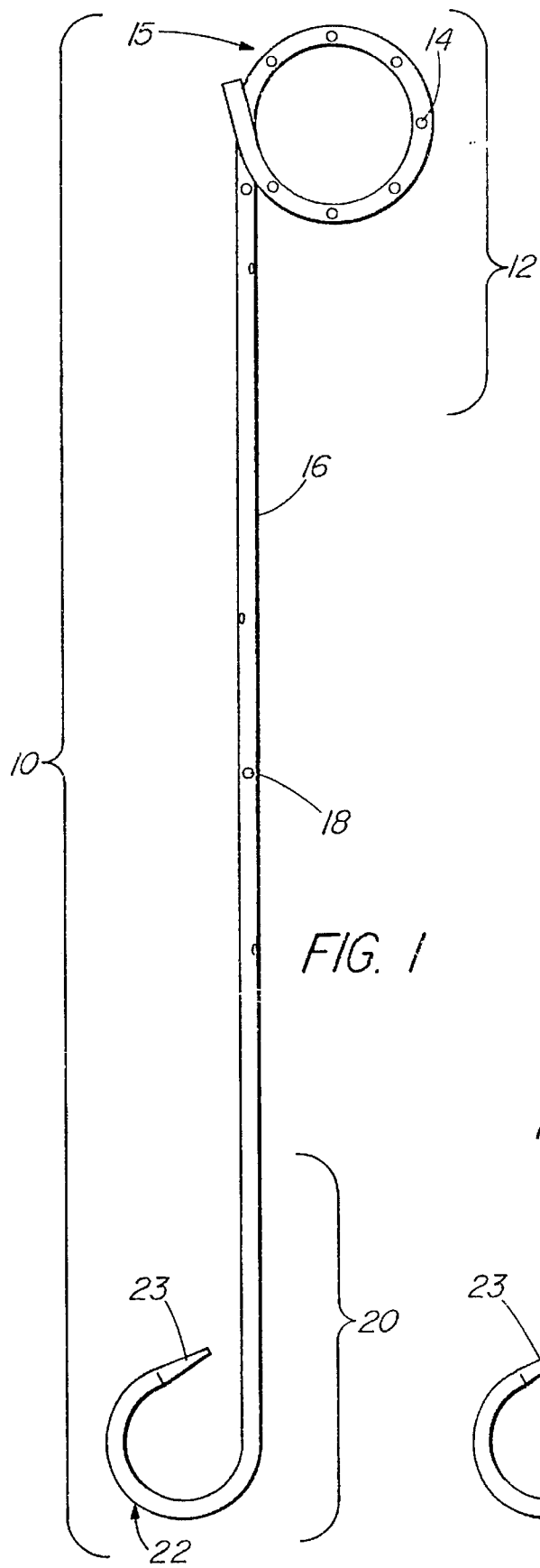
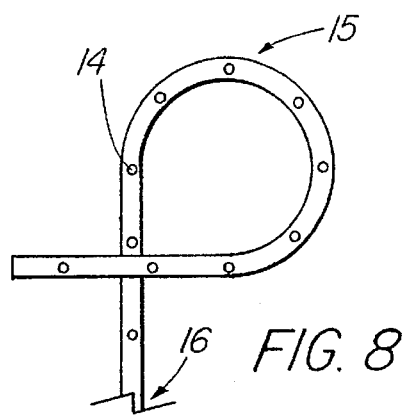
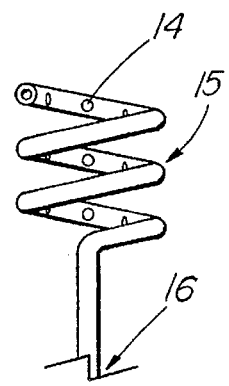
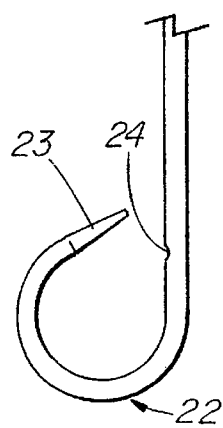
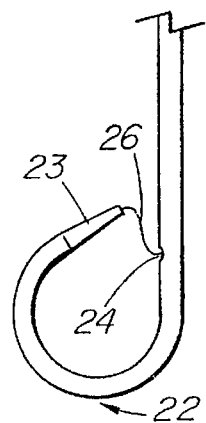

ANTI-REFLUX URETERAL STENT

TECHNICAL FIELD

This inventions relates to an indwelling ureteral stent or drainage tube placed between the kidney and the bladder. More particularly, the stent provides for enhanced drainage between the kidney and bladder while inhibiting the backflow or reflux of urine into the kidney from the bladder in order to reduce the risk of sepsis, pain and urinary leakage.

BACKGROUND OF THE INVENTION

Indwelling ureteral stents are in common use today. These stents are placed in the ureter which is the duct between the kidney and the bladder, for establishing and/or maintaining an open patent flow of urine from the kidney to the bladder. The predominate indications for placing a ureteral stent include extrinsic compression, ureteral injury due to trauma, obstructive uropathy, and following surgery in the upper or lower urinary tract. Generally, the stent is comprised of a flexible material having sufficient resiliency to allow it to be straightened for insertion into the body passageway, while having sufficient memory to return to its predetermined retentive shape when in situ.

Indwelling ureteral stents are positioned in the ureter by various procedures including, antegrade (percutaneous) placement, retrograde (cystoscopic) placement through the urethra, as well as by open ureterotomy or surgical placement in the ureter under direct visual placement. Ureteral stent positioning may be accomplished by several methods. One method, a wire guide is introduced into the ureteral orifice in the bladder via a cystourethroscope under direct vision. A wire guide is advanced up the ureter until the advancing flexible tip of the guide is confirmed by x-ray or fluoroscopy to be in the renal pelvis of the kidney. A tubular stent with both ends open is fed into the exposed external segment of the wire guide and advanced over the wire guide by hand until a short segment of the stent is visible outside the cystourethroscope. A pusher catheter, "positioner" or length of the tubing is then fed into the exposed external end of the wire guide and advanced over the wire guide by hand until it abuts against the stent. With the wire guide held stationary, the positioner is advanced over the wire guide to push the tubular stent up the ureter to the renal pelvis. With the anatomical proximal end of the stent in the renal pelvis, positioner is held stationary while the wire guide is gradually extracted from the stent and the positioner. As the wire guide leaves the proximal end of the tubular stent, the retentive means of the proximal end of the stent is formed to retain the stent in the pelvis of the kidney. As the wire guide is withdrawn past the distal or intravesical, end of the stent, retentive hook or curve of the distal end is formed so that the stent is retained within the bladder. At this point, the positioner and wireguide are completely withdrawn leaving only the stent indwelling in the ureter, bladder and kidney.

In another method of ureteral stent placement, a ureteral stent having one tip closed is backloaded into the wire guide. In this "pushup" method, the tip of the wireguide contacts the closed tip of the ureteral stent, which is then introduced into the ureteral orifice in the bladder via a cystourethroscope under direct vision. The stent is advanced up the ureter under fluoroscopic control until the tip of the stent lies within the renal pelvis. A positioner catheter or length of tubing is fed into the external end of the wireguide and advanced over the wireguide by hand until it butts against the open, distal end of the stent. In yet another method, a single invasive entry into the ureteral orifice and ureter is disclosed in U.S. Pat. No. 4,957,479.

One of the problems with this procedure and the implantation of such ureteral stents is when sufficient pressure builds in the bladder, a back flow, or a reflux of urine may occur into the kidney. Where there is no infection or pyrogenic organism present, this is not a problem since the urine is generally considered a sterile fluid within the body. However, in the event of the presence of infection or pyrogenic organisms, possibility of reflux may result in the development of sepsis which is potentially lethal and generally, most prevalent in the elderly. The risk of sepsis increases with the employment of such urinary drainage stents and catheters, particularly in the ureter between the kidney and the bladder. In view of the foregoing, there is a need to provide a ureteral stent which will be beneficial in establishing and/or maintaining an open patent flow of urine from the kidney to the bladder while inhibiting the backflow or reflux of urine to the kidney.

SUMMARY OF THE INVENTION

In accordance with the present invention, a ureteral stent is provided for implantation in the ureter between the bladder and kidney to provide drainage of urine from the kidney to the bladder in the event of a blockage while inhibiting reflux of urine into the ureter and kidney in order that the patient would not develop sepsis in the event of a bladder infection and the like. The stent comprises an elongated tubular body having two end sections, a bladder end section and a kidney end section, retention means at each of the end sections, fluid passageways incorporated in the kidney end section and along the length of the tubular body, and a closed bladder end section that does not include fluid passageways.

In the past, stents of this nature for implanting in the ureter, have had two open ends which while effective for drainage of the urine from the kidney to the bladder in the event of an obstruction or blockage, had the problem of allowing urine to reflux back into the ureter and kidney when there is a sufficient build up of pressure within the bladder. While urine is generally considered to be sterile when it is within the body, in the event the patient in which the stent is implanted has a bladder infection or otherwise has pyrogens present in the urine, the reflux of urine from the bladder into the ureter and kidney would introduce this infection into the kidney causing the patient to develop sepsis which is potentially lethal, particularly in the elderly or very young.

The stent may be derived from any number of flexible materials and preferably various elastomeric materials. The stent may also be produced in varying lengths and lumen diameters.

Further in accordance to the present invention, the stent may include any number of retention means in order to insure that the stent remains in place and not migrate out of the bladder and/or kidney. Moreover, the retention means in the bladder end section may take the shape of a "J" and may be locked in place after implantation by a variety of mechanisms.

Still further in accordance with the present invention, this stent may be implanted by a number of known techniques which generally include placing the stent over a wireguide and using a cystoscope and a positioning catheter in order to position the stent in the bladder and ureter and kidney.

These and other aspects of the invention will be come clear to those skilled in the art upon the reading and understanding of the specification that follows.

BRIEF DESCRIPTION OF THE DRAWINGS

The invention will be further described in connection with the attached drawing figures showing preferred embodiments of the invention including specific structural features and mechanisms. It is intended that the drawings included as a part of this specification be illustrative of the preferred embodiment of the invention and should in no way be considered as a limitation on the scope of the invention.

FIG. 1 is a perspective view of one embodiment of the ureteral stent in accordance with the present invention.

FIG. 2 shows one embodiment of the bladder end section of the ureteral stent in accordance with the present invention.

FIG. 3 shows one embodiment of a locking in the tip for the bladder end section of the ureteral stent according to the present invention.

FIG. 7 shows the kidney end section illustrating one embodiment of a retention means in accordance with the present invention.

FIG. 8 shows a kidney end section illustrating still another embodiment of a retention means for the ureteral stent in accordance with the present invention.

DETAILED DESCRIPTION OF THE PREFERRED EMBODIMENTS

Figure 4:
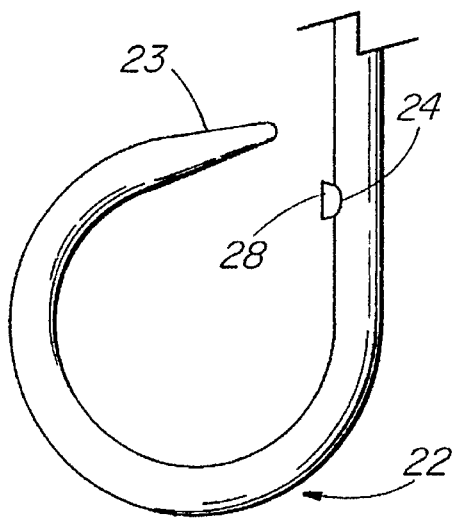
FIG. 4 shows an embodiment for plugging the single fluid passageway incorporated in the bladder end section of the ureteral stent according to the present invention.

For the purposes of promoting and understanding of the principles of the invention, reference will now be made to the embodiments illustrated in the drawings and specific language will be used to describe these embodiments. It should nevertheless be understood that no limitation of the scope of the invention is intended by this description and such alterations and further modifications in the illustrated device, and such further applications of the principles of the dimensions illustrated in the description that follows being contemplated as would normally occur to one skilled in the art to which the invention relates.

Referring now to FIG. 1, a perspective view of one embodiment of the ureteral stent 10 according to the present invention is illustrated. The ureteral stent 10 is an elongated tubular body having two end sections 20 and 12 where the kidney end section 12 comprises a pigtail shaped retention means 15 and fluid passageways 14. The bladder end section 20 comprises the J-shaped retention means 22 including tip 23. The stent 10 also includes straight section 16 and fluid passageways 18 which, in this particular embodiment, are spiraled along a portion of the length of straight section 16. The stents are produced from flexible material which is preferably elastomeric and containing memory in order that any portion of the stent which is curved will return to its original shape if straightened during the implantation procedure. The polymers or elastomers from which the stent is produced are radiopaque and preferably are C-FLEX®-TPE, a terpolymer of styrene-ethylene-butadiene-styrene commercially available through Concept Polymer Technologies, a rigid polyurethane, Sof-Flex®, a soft polyurethane and silicone based polymers.

The ureteral stent according to the present invention is designed to preferably have a length of about 8 cm to about 30 cm and having outer diameters in the range of about 1 mm to about 4 mm. Most preferably, the outer diameters of the stents according to the present invention range from about 1.5 mm to about 3 mm and most preferably the stent will have a wall thickness in the range of about 0.25 mm to about 1 mm.

As illustrated in FIG. 1, the fluid passageways 14 and 18 are located in the kidney end section as well as a portion of the straight section 16 of the stent. The bladder end section is closed and either contains no fluid passageways or contains one for running a lead through and potentially locking the tip of the bladder end section into, but will be closed or plugged upon the implantation of the stent. The diameter of these fluid passageways may be no greater than the diameter of the lumen of the stent and may be of any shape, but preferably round. In a preferred embodiment of the present invention, fluid passageways are incorporated in the stent from about ⅔ the distance from the kidney end section to about ¾ the distance from the kidney end section of the ureteral stent according to the invention. For example, a 20 cm stent would contain fluid passageways from about 13 cm to about 15 cm along the straight section of the stent where the remaining or bladder end section 20 of 5 cm to about 7 cm would not contain any fluid passageways.

In still another embodiment according to the present invention, the bladder end section 20 may contain a single passageway in the straight portion of the stent and aligned with the tip of the bladder end section retention means such that when the retention means is in the shape of a J and completely coiled, the tip will insert and lock into the fluid passageway. One such embodiment of this locking mechanism is illustrated in FIG. 2 wherein the memory of the elastomeric material would receive the closed end tip of this bladder end section retention means 22 automatically when the coil was unrestrained. Also, the tip 23 of the coiled retention means 22 of bladder end section 20 is preferably tapered in order that the tip 23 will fit snugly into fluid passageway 24. The fluid passageway 24 may also serve the purpose for the insertion and placing the stent over a guidewire.

Another embodiment of the J coiled retention means 22 for bladder end section 20 is illustrated in FIG. 3 where the tip contains a tether or possibly an integral tether which may run through the closed end section along the length of the stent exiting at the kidney end section in order that the tip 23 of the J-shaped retention means 22 may be pulled into the fluid passageway 24 and secured.

Figure 5:
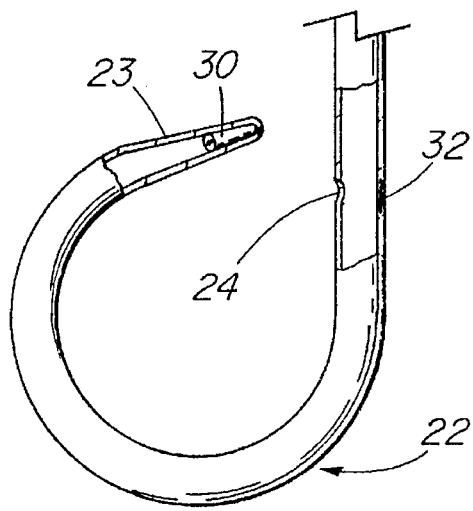
FIG. 5 shows the bladder end section in a partial sectional view illustrating still another embodiment of a locking mechanism for the bladder end section of the ureteral stent according to the present invention.

A still further embodiment according to the present invention is illustrated in FIG. 4, where the fluid passageway 24 in the bladder end section 20 may be plugged with a stopper 28 as opposed to inserting the tip 23 into fluid passageway 24. A further variation of this embodiment is illustrated in FIG. 5 showing the tip 23 of the J-shaped retention means 22 containing a permanent magnet 30 and the straight section which includes fluid passageway 24 also contains a permanent magnet 32 or magnetic material incorporated in the polymer matrix such that the tip is attracted to and will be forced into the fluid passageway 24 to give a closed bladder end section 20. Another embodiment for forming the retention means 22 of bladder end section 20 may include forming the bladder end section from a material having high memory, e.g., superelastic Nitinol (not shown), such that it will quickly return to its original shape and strongly retain the original shape. Or the fluid passageway may include a one-way valve such that fluid may not escape through fluid passageway 24.

Both the bladder end section 20 and kidney end section 12 may include retention means 22 and 15 of varying shapes and designs, for example, a FIG. 4, as illustrated in FIG. 8, and a helical coil as illustrated in FIG. 7.

Figure 6:
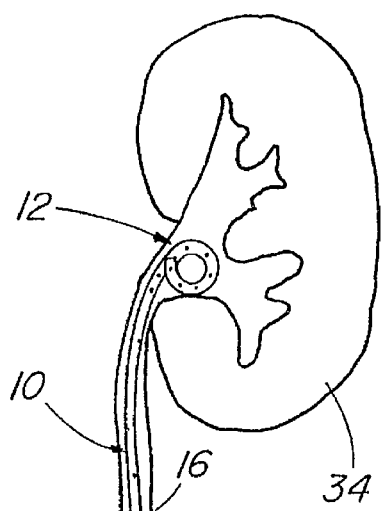
FIG. 6 is a perspective view of the stent according to one embodiment of the invention in the configuration it assumes indwelling in the kidney, ureter, and bladder of a patient.

As previously indicated, stents may be implanted or placed in the ureter by various techniques or procedures. In a preferred embodiment, the stent 10 is placed over a guidewire and followed by the stent being placed through a cystoscope and up into the ureter. In another procedure, a wireguide may be first placed through a cystoscope and into the urethra up into the ureter and into the kidney. The stent 10 is then fed onto the guidewire and over the guidewire until the retention means 15 has formed in the kidney. A positioning catheter may be used to place the stent in this procedure where it is stabilized in the bladder and the wireguide is removed from the stent. The positioning catheter is then removed along with the guidewire. A properly positioned ureteral stent according to the present invention is illustrated in FIG. 6, showing the bladder end section 20 positioned and retained in the bladder 38 and the kidney end section 12 positioned and retained in the kidney 34 where the straight section 16 is located in the ureter 36.

While the invention has been illustrated and described in detail in the drawings and foregoing description, the same is to be considered as illustrative and not restrictive in character. It should be understood that only the preferred embodiments have been shown and described, and that all changes and modifications that come within the spirit of the invention fall within the scope of the claims that follow.

What is claimed is:

1. A ureteral stent for implantation between a bladder and a kidney to prevent reflux of urine into the kidney, comprising:

an elongated tubular body having multiple sections including:
      a bladder end section defined by that sections of said elongated tubular body in the bladder when said stent is positioned in a patient,
      a kidney end section, and
      a straight section connecting the bladder end section and the kidney end section,
   wherein the bladder end section and the kidney end section each includes retention means at an end thereof, fluid passageways incorporated in the kidney end section and along a length of the straight section, wherein no fluid passageways are incorporated in the bladder end section and along a portion of the straight section connecting the bladder end section, and wherein the bladder end section is closed.

2. The stent according to claim 1 wherein the bladder end section contains a single fluid passageway in the straight section of said elongated tubular body and wherein said bladder end section includes a tip at the terminus of the bladder end section aligned such that the tip of the bladder end section is inserted in said single fluid passageway when said bladder end section is coiled and closed.

3. The stent according to claim 2 wherein said bladder end section further comprises a tether that may be ligated around the stent upon inserting the tip of the bladder end section into said single fluid passageway.

4. The stent according to claim 3 comprising an integral tether contained within the lumen of the bladder end section and running the entire length of said stent to provide a means to pull the tip of said bladder end into the single passageway in the straight segment of said bladder end section and to secure said tip of said bladder end section into said single passageway.

5. The stent according to claim 2 wherein said single fluid passageway contained within the bladder end section comprises a one-way valve, is derived from a superelastic alloy of nickel and titanium, is closed by a stopper after implantation, or wherein the tip of said bladder end section comprises a permanent magnet and said straight section of said bladder end section comprises a permanent magnet of opposite polarity to attract said tip of said bladder end section into said single passageway.

6. The stent according to claim 1 wherein said stent is from about 8 cm to about 30 cm in length and having a diameter of from about 1 mm to about 4 mm.

7. The stent according to claim 6 wherein said stent has a diameter from about 1.5 mm to about 3 mm and wherein a wall thickness of said stent ranges from about 0.25 mm to about 1 mm.

8. The stent according to claim 1 wherein the diameter of said fluid passageways is no greater than the diameter of the lumen of the stent.

9. The stent according to claim 1 wherein said fluid passageways are terminated at two-thirds of the length of the stent measured from the kidney end section of the stent.

10. The stent according to claim 1 wherein said fluid passageways are terminated at three-quarters of the length of the stent measured from the kidney end section of the stent.

11. The stent according to claim 1 wherein said stent is derived from a flexible elastomeric material selected from the group consisting essentially of a styrene-ethylene-butadiene terpolymer, a rigid polyurethane, a soft polyurethane, or a silicon based polymer.

12. The stent according to claim 11 wherein said flexible elastomeric material is radiopaque.

13. The stent according to claim 1 wherein said retention means has a form selected from the group consisting essentially of a pigtail, a coil, a "J", and a figure four.

14. A ureteral stent for implantation between a bladder and a kidney to prevent reflux of urine into the kidney, comprising:

an elongated tubular body having multiple sections including:
      a bladder end section defined by that sections of said elongated tubular body in the bladder when said stent is positioned in a patient,
      a kidney end section, and
      a straight section connecting the bladder end section and the kidney end section,
   wherein the bladder end section and the kidney end section each includes retention means at an end thereof, fluid passageways incorporated in the kidney end section and along a length of the straight section, wherein no fluid passageways are incorporated in the bladder end section and along a portion of the straight section connecting the bladder end section and such fluid passageways are terminated at ⅔ of the length of the stent measured from the kidney end section, and the bladder end section is closed, and wherein said stent is from about 8 cm to about 30 cm in length and having a diameter of about 1 mm to about 4 mm and further wherein the retention means of the kidney end section takes a form of a pigtail.

* * * * *